United States Patent [19]
Ransohoff et al.

[11] Patent Number: 5,977,334
[45] Date of Patent: Nov. 2, 1999

[54] DNA ENCODING A CHEMOKINE, BETA R1, COMPRISING THE BETA R1 PROMOTER

[75] Inventors: Richard Ransohoff, Shaker Heights; Sandhya Rani, South Euclid, both of Ohio

[73] Assignee: The Cleveland Clinic Foundation, Cleveland, Ohio

[21] Appl. No.: 08/927,722

[22] Filed: Sep. 11, 1997

[51] Int. Cl.⁶ .......................... C12N 15/19; C07K 14/52
[52] U.S. Cl. ............... 536/23.51; 536/24.1; 435/69.5; 435/320.1
[58] Field of Search .................. 536/23.51, 24.1; 435/320.1, 69.5

[56] References Cited

U.S. PATENT DOCUMENTS 5,707,829  1/1998  Jacobs et al. .......................... 435/69.1

OTHER PUBLICATIONS

"Characterization of β–R1, a Gene that is Selectively Induced by Interferon β (IFN–β) compared with IFN–α*", Rani, et al., *The Journal of Biological Chemistry*; vol. 271, No. 37, Sep. 13, 1996; pp. 22878–22884.

*GenBank Accession*, U59286; Oct. 24, 1996.

*Primary Examiner*—David L. Fitzgerald
*Attorney, Agent, or Firm*—Calfee, Halter & Griswold LLP

[57] ABSTRACT

The invention provides a chemokine designated Beta R1, whose production in T cells, astrocytes, a fibroblasts is preferentially induced by IFN-β as compared to IFN-α. A cDNA encoding the Beta R1 polypeptide and comprising the endogenous Beta R1 promoter is described. When coupled to a reporter gene, the promoter sequence may be used to screen for mimics of IFN-β activity.

12 Claims, 6 Drawing Sheets

VI LCATVVQGFP MFKRGRCLCI GPGVKAVKVA

DIEKASIMYP SNNCDKIEVI ITLKENKGQR CLNPKSKQAR LIIKKVERKN

QQQQKTNMSV KGMAIALAVI LCATVVQGFP MFKRGRCLCI GPGVKAVKVA

DIEKASIMYP SNNCDKIEVI ITLKENKGQR CLNPKSKQAR LIIKKVERKN

ORF Start
↓
GCAGCAAC AGCAAAAAAC AAACATGAGT GTGAAGGGCA TGGCTATAGC
CGTCGTTG TCGTTTTTTG TTTGTACTCA CACTTCCCGT ACCGATATCG CTTGGCTGTG ATATTGTGTG CTACAGTTGT TCAAGGCTTC CCCATGTTCA
GAACCGACAC TATAACACAC GATGTCAACA AGTTCCGAAG GGGTACAAGT AAAGAGGACG CTGTCTTTGC ATAGGCCCTG GGGTAAAAGC AGTGAAAGTG
TTTCTCCTGC GACAGAAACG TATCCGGGAC CCCATTTTCG TCACTTTCAC GCAGATATTG AGAAAGCCTC CATAATGTAC CCAAGTAACA ACTGTGACAA
CGTCTATAAC TCTTTCGGAG GTATTACATG GGTTCATTGT TGACACTGTT AATAGAAGTG ATTATTACCC TGAAAGAAAA TAAAGGACAA CGATGCCTAA
TTATCTTCAC TAATAATGGG ACTTTCTTTT ATTTCCTGTT GCTACGGATT ATCCCAAATC GAAGCAAGCA AGGCTTATAA TCAAAAAAGT TGAAAGAAAG
TAGGGTTTAG CTTCGTTCGT TCCGAATATT AGTTTTTTCA ACTTTCTTTC ORF Ends
　　　↓
AATTTTTAAA
TTAAAAATTT

Fig. 2

```
CANAACTGGA CTCGCGCGCC TGCAGGTCGA CACTAGTGGA TCCAAAGAAT
GTNTTGACCT GAGCGCGCGG ACGTCCAGCT GTGATCACCT AGGTTTCTTA

Transcription Start Site
                    ↓
TCGGCACGAG CCAAGAAAGA CGAGCAAAGC TGAAGTAGCA GCAACAGCAC
AGCCGTGCTC GGTTCTTTCT CGTCGTTTCG ACTTCATCGT CGTTGTCGTG ORF Start
      ↓
CAGCAGCAAC AGCAAAAAAC AAACATGAGT GTGAAGGGCA TGGCTATAGC
GTCGTCGTTG TCGTTTTTTG TTTGTACTCA CACTTCCCGT ACCGATATCG CTTGGCTGTG ATATTGTGTG CTACAGTTGT TCAAGGCTTC CCCATGTTCA
GAACCGACAC TATAACACAC GATGTCAACA AGTTCCGAAG GGGTACAAGT AAAGAGGACG CTGTCTTTGC ATAGGCCCTG GGGTAAAAGC AGTGAAAGTG
TTTCTCCTGC GACAGAAACG TATCCGGGAC CCCATTTTCG TCACTTTCAC GCAGATATTG AGAAAGCCTG CATAATGTAC CCAAGTAACA ACTGTGACAA
CGTCGATAAC TCTTTCGGAG GTATTACATG GGTTCATTGT TGACACTGTT AATAGAAGTG ATTATTACCC TGAAAGAAAA TAAAGGACAA CGATGCCTAA
TTATCTTCAC TAATAATGGG ACTTTCTTTT ATTTCCTGTT GCTACGGATT ATCCCAAATC GAAGCAAGCA AGGCTTATAA TCAAAAAAGT TCAAAGAAAG
TAGGGTTTAG CTTCGTTCGT TCCGAATATT AGTTTTTTCA ACTTTCTTTC ORF Ends
       ↓
AATTTTTAAA AATATCAAAA CATATGAAGT CCTGGAAAAG GCATCTGAA
TTAAAAATTT TTATAGTTTT GTATACTTCA GGACCTTTTC CCGTAGACTT
```

Fig. 4

```
AAACCTAGAA CAAGTTTAAC TGTGACTACT GAAATGACAA GAATTCTACA
TTTGGATCTT GTTCAAATTG ACACTGATGA CTTTACTGTT CTTAAGATGT

GTAGGAAACT GAGACTTTTC TATGGTTTTG TGACTTTCCA CTTTTGTTCA
CATCCTTTGA CTCTGAAAAG ATACCAAAAC ACTGAAAGGT GAAAACAAGT

GTTATTTGAA GGATGAAAGG TGGGTGAAAG GACCCAAAAC NGAAATACGT
CAATAAACTT CCTACTTTCC ACCCACTTTC CTGGGTTTTG NCTTTATGCA

CTCCCTGAAT GAATGACAAT CCGAATCCNC TGCCCCAAAG AATCCCACNA
GAGGGACTTA CTTACTGTTA GGCTTAGGNG ACGGGGTTTC TTAGGGTGNT

TTTAATGGAT TCNTAGGAAA ACTACCTTAN AAAGGCNGGT TACCTCCGAA
AAATTACCTA AGNATCCTTT TGATGGAATN TTTCCGNCCA ATGGAGGCTT

TTTACCAAGT GCNTCCCTTT CCTACTTGTT GTTTTATACT TCCNGCNTTC
AAATGGTTCA CGNAGGGAAA GGATGAACAA CAAAATATGA AGGNCGNAAG

CTAGGCNAN
GATCCGNTN
```

Fig. 4 (con't)

Fig.5

DNA ENCODING A CHEMOKINE, BETA R1, COMPRISING THE BETA R1 PROMOTER

CHEMOKINES AND PROMOTERS RESPONSIVE TO BETA INTERFERON

This invention was made in part with United States government support under grant number PO1CA 62220 awarded by the National Cancer Institute. The U.S. government has certain rights in the invention.

BACKGROUND OF THE INVENTION

Interferon (IFNs) are a family of cytokines with diverse biological functions, including antitumor, immunomodulatory, antiviral and antiparasitic actions. At present, the IFN family includes more than 20 different proteins. Initially, IFN's were classified by source as leucocyte, fibroblast, or immune IFNs. Initially, IFNs were also grouped into two types with Type 1 comprising fibroblast and leucocyte IFNs and type II comprising immune IFNs. Based on their genetic similarities and differences, the type I IFNs are currently divided into the following three classes: IFN-$\alpha$, IFN-$\beta$, and IFN-$\omega$. The type II IFNs are classified as IFN-$\gamma$.

IFNs act by binding to specific cell receptors, which are found on the surface of most cells, and causing the translocation to the nucleus of cytoplasmic transcription factors that enhance or suppress the expression of specific genes. The products of these interferon-stimulated genes (hereinafter referred to as ISGs) are primarily polypeptides that act as mediators of the biological activities associated with the respective IFN. IFN-$\alpha$ and IFN-$\beta$ bind to the same receptor and activate transcription of ISGs through the assembly and translocation from the cytoplasm to the nucleus of ISGF3, a multisubunit transcription factor that interacts with a cis-acting DNA regulatory element termed the interferon-stimulated response element or ISRE. Transcription of the ISGs stimulated by IFN-$\alpha$ and IFN-$\beta$ occurs in the absence of ongoing protein synthesis, and is therefore mediated directly by the interaction of either IFN-$\alpha$ or IFN-$\beta$ with their common receptor.

IFN-$\beta$ is a particularly useful cytokine which has been shown to be effective in decreasing the relapse rate, relapse severity, progression of neurological disability and development of new brain lesions, as observed with brain magnetic resonance imaging, in relapsing-remitting multiple sclerosis patients. Unfortunately, IFN-$\beta$ can cause side effects in such patients. Moreover, a substantial number of the patients treated with IFN-$\beta$ develop neutralizing antibodies. In addition, IFN-$\beta$ must be administered by injection. There are also concerns that IFN-$\beta$ may not penetrate certain tissue compartments Accordingly, efforts are currently underway to identify other compounds, particularly small molecular weight molecules, that induce an IFN-$\beta$ type response, hereinafter referred to as "IFN-$\beta$ mimics". These efforts are directed at identifying IFN-$\beta$ mimics that can be administered orally and that freely permeate tissues. The efforts are also directed at identifying IFN-$\beta$ mimics that are less toxic than naturally-occurring or recombinant forms of IFN-$\beta$.

In certain instances, such as autoimmune diseases, IFN-$\alpha$ or IFN-$\beta$ can induce a deleterious inflammatory reaction in an individual. Accordingly efforts are also underway to identify compounds, hereinafter referred to as "IFN-$\beta$ inhibitors", that block the IFN-$\beta$ type components of this reaction.

The efforts to identify IFN-$\beta$ mimics and IFN-$\beta$ inhibitors have been hampered by the fact that there are no known ISG products whose synthesis is selectively induced by IFN-$\beta$ as compared to IFN-$\alpha$ and thus can be used to give the full measure of an IFN-$\beta$ type response. Accordingly, it is desirable to have an ISG product whose synthesis is selectively induced by IFN-$\beta$ as compared to IFN-$\alpha$. It is also desirable to have a system that can be used to identify compounds that selectively induce an IFN-$\beta$ type response as compared to an IFN-$\alpha$ type response. An in vitro system that can be used to screen IFN-$\beta$ mimics and that can be used to assess the potency of the IFN-$\beta$ mimics is especially desirable. It is also desirable to have a system that can be used to screen IFN-$\beta$ inhibitors.

SUMMARY OF THE INVENTION

The present invention provides a system for screening IFN-$\beta$ mimics or IFN-$\beta$ inhibitors The system comprises a polynucleotide that comprises a DNA sequence encoding a unique chemokine promoter, hereinafter referred to as the "Beta R1 promoter", operatively linked to a reporter gene that encodes an assayable product.

The present invention also provides a method of employing the system to assay the concentration of IFN-$\beta$ in a sample and to screen putative IFN-$\beta$ mimics. In one embodiment, the method comprises the steps of providing cultured cells transfected with a polynucleotide construct that comprises a DNA sequence that encodes the Beta R1 promoter operatively linked to a reporter gene that encodes an assayable product; treating the transfected cells with the putative IFN-$\beta$ mimic or the sample; detecting the assayable product produced by the treated cells. Synthesis of the assayable product by the cells treated with the putative IFN-$\beta$ mimic or the sample is indicative of the IFN-$\beta$ response. In another embodiment, the method comprises the steps of treating a group of cultured cells with the putative IFN-$\beta$ mimic or sample and detecting the presence of the Beta R1 transcript in the treated cells; wherein the presence of the Beta R1 transcript in the treated cells is indicative of the IFN-$\beta$ response.

The present invention also provides an isolated Beta R1 polypeptide, whose production is selectively induced by IFN-$\beta$ as compared to IFN-$\alpha$. The Beta R1 polypeptide is an inducible CXC, non-ELR chemokine whose expression is stimulated in T cells, astrocytes, and fibroblasts that have been exposed to IFN-$\beta$. The present invention also provides an isolated polynucleotide that encodes the Beta R1 polypeptide.

DETAILED DESCRIPTION OF THE INVENTION

The Beta R1 Polypeptide

In accordance with one aspect of the present invention a unique polypeptide, Beta R1, is provided. The mature form of the Beta R1 polypeptide has a calculated molecular weight of about 9 kDa. Based on its structural characteristics, e.g., its size and the presence of four cysteine residues in the highly conserved positions characteristic of chemokines, and its induction by IFNs, the Beta R1 polypeptide is a chemokine. The two cysteine residues nearest the N-terminus of the Beta R1 polypeptide have an amino acid therebetween. The Beta-R1 polypeptide also lacks a glutamic acid-leucine-arginine (ELR) sequence between the N-terminus and the first cysteine. Thus, the Beta R1 polypeptide belongs to the CXC, non-ELR subfamily of chemokines. Other members of this subfamily include. IP-10, MIG-8 and SDF1α. The Beta R1 polypeptide shown in FIG. 1A, SEQ.ID. NO.3, shares 31% amino acid identity with IP-10. Allowing for conservative substitutions, this Beta R1 polypeptide and IP-10 share 55% amino acid identity. As with other chemokines in the CXC, non-ELR family, the Beta R1 polypeptide may be used as an angiostatic agent, as an anti-tumor agent, or to promote wound healing.

The Beta R1 gene is selectively transcribed in fibroblasts, T-cells, and astrocytes in response to treatment with IFN β as compared to IFN α. The Beta R1 transcript is detectable by Northern blot analysis within 4 to 8 hours of induction by IFN-β. Thus, the mRNA molecules that encode the Beta R1 polypeptide and the Beta R1 polypeptide itself are selective markers of the IFN-β response.

Figure 1A:
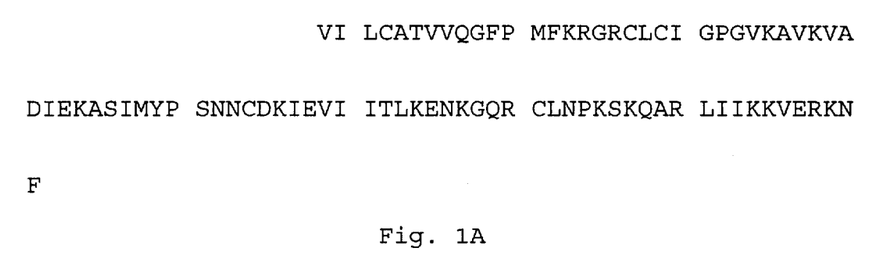
FIG. 1A depicts the amino acid sequence, SEQ ID NO: 3, of the human Beta R1 polypeptide.

In one embodiment the mature human Beta R1 polypeptide has the amino acid sequence shown in FIG. 1A (SEQ ID NO: 3). In other embodiments the Beta RI polypeptide comprises an allelic variant or a derivative of the amino acid sequence shown in FIG. 1A. The Beta R1 polypeptide may be in the form of a prepolypeptide wherein the prepolypeptide further comprises a leader or secretory sequence. One embodiment of the human Beta R1 prepolypeptide appears in FIG. 1B, SEQ. ID. NO. 2. The Beta R1 polypeptide may be in the form of a fusion protein wherein additional amino acids which aid in, for example, purification of the polypeptide are fused to the mature or prepolypeptide form of Beta R1 at either the 3' or 5' end thereof. In addition to naturally occurring allelic forms of the polypeptide, the Beta R1 polypeptide as described herein embraces non-naturally occurring allelic forms of the Beta R1 polypeptide where one or more of the amino acids have been replaced by conservative amino acid residues, typically by using direct synthesis or recombinant techniques. More preferably, the Beta R1 polypeptide is provided in an isolated form. Preferably, the Beta R1 polypeptide is purified.

Preparing the Polypeptide

The Beta R1 polypeptide can be synthetically produced by conventional peptide synthesizers. The Beta R1 polypeptide can also be produced using cell-free translation systems and RNA molecules derived from DNA constructs that encode the Beta R1 polypeptide. Alternatively, the Beta R1 polypeptide can be made by transfecting host cells with expression vectors that comprise a DNA sequence which encodes the Beta R1 polypeptide and then inducing expression of the polypeptide in the host cells.

The Beta R1 polypeptide can be expressed in suitable host cells, such as for example, mammalian cells, yeast, bacteria, or other cells under the control of appropriate promoters. Following transformation of the suitable host strain and growth of the host strain to an appropriate cell density, the cells are typically harvested by centrifugation, disrupted by physical or chemical means, and the resulting crude extract retained for further purification of the Beta R1 polypeptide.

The recombinant Beta R1 polypeptide that is expressed in a host cell culture is usually isolated by initial extraction from cell pellets or from cell culture medium, followed by salting-out, and one or more chromatography steps, including aqueous ion exchange chromatography, size exclusion chromatography steps, and high performance liquid chromatography (HPLC).

The Beta R1 Polynucleotide

In accordance with another aspect of the present invention, there is provided a polynucleotide that encodes the Beta R1 polypeptide. The polynucleotide may be single stranded or double stranded. The polynucleotide may be a DNA or RNA molecule, preferably a DNA molecule, and comprises a sequence which codes for the Beta R1 polypeptide, preferably the human Beta R1 polypeptide. Preferably, the polynucleotide encodes at least the mature form of the Beta R1 polypeptide. The polynucleotide may also comprise a leader sequence and encode a Beta R1 prepolypeptide which is processed and secreted from mammalian cells as the mature polypeptide. The polynucleotide of the present invention may also be fused in frame to a marker sequence which allows for purification of the Beta R1 polypeptide.

Figure 4:
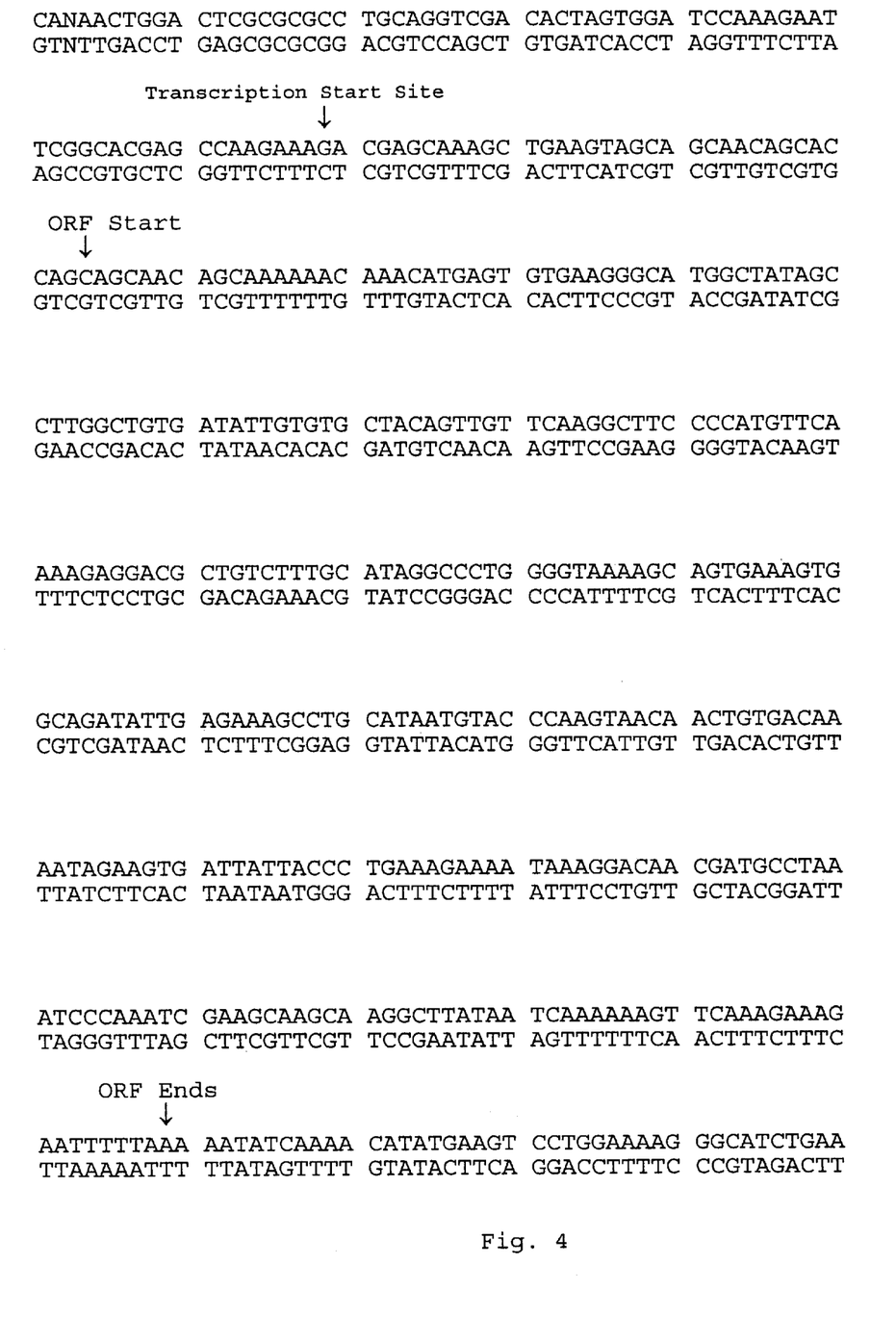
FIG. 4 depicts a portion of the nucleotide sequence of the cDNA insert of pCB-R1-a11.

In one embodiment, the polynucleotide encodes for a polypeptide comprising the amino acid sequence shown in FIG. 1A, SEQ. ID. NO. 3 In other embodiments, the polynucleotide encodes the amino acid sequence shown in FIG. 1B, SEQ. ID. NO.2, or an allelic variant of the polypeptide comprising the amino acid sequences shown in FIG. 1A, SEQ. ID. NO. 3 and FIG. 1B, SEQ. ID. NO. 2. One example of a polynucleotide that encodes the polypeptides of SEQ. ID. NO. 2 and SEQ. ID. NO.3, is depicted in FIG. 4, SEQ. ID. NO. 1. The present invention further relates to polynucleotides which are complementary to the herein above-described sequences and to sequences that have at least 80% and preferably 90% identity with the herein above-described sequences or sequences that are complementary thereto. The polynucleotide of the present invention further relates to polynucleotide sequences which hybridize under stringent conditions to the hereinabove-described polynucleotide sequences. Defining stringent condition is within the skill of the art. As herein used, the term "stringent conditions" means hybridization will occur if there is at least 95% and, preferably, at least 97% identity between the sequences. Preferably, the polynucleotide is provided in an isolated form.

The polynucleotide of the present invention may be employed for producing a Beta R1 polypeptide by recombinant techniques. Thus, for example, the polynucleotide sequence may be introduced into an expression vector. Suitable expression vectors include for example chromosomal, nonchromosomal and synthetic DNA sequences, e.g., derivatives of SV40, bacterial plasmids, phage DNA's; yeast plasmids, vectors derived from combinations of plasmids and phage DNAs, viral DNA such as vaccinia, adenovirus, fowl pox virus, and pseudorabies. The DNA sequence is introduced into the expression vector by conventional procedures.

Accordingly, the present invention also relates to recombinant constructs comprising one or more of the sequences as broadly described above. The constructs can be in the form of a vector, such as a plasmid, phagemid, or viral vector, into which a sequence that encodes the Beta R1 polypeptide has been inserted.

In the expression vector, the DNA sequence which encodes Beta R1 is operatively linked to an expression control sequence, i.e., a promoter, which directs mRNA synthesis. Representative examples of such promoters, include the LTR or SV40 promoter, the E coli lac or trp, the phage lambda PL promoter and other promoters known to control expression of genes in prokaryotic or eukaryotic cells or in viruses. The promoter may also be the natural promoter of the Beta R1 coding sequence. The expression vector also contains a ribosome binding site for translation initiation and a transcription terminator. Preferably, the recombinant expression vectors also include an origin of replication and a selectable marker, such as for example, the ampicillin resistance gene of E. coli to permit selection of transformed cells, i.e. cells that are expressing the heterologous DNA sequences.

The polynucleotide sequence encoding the Beta R1 polypeptide is incorporated into the vector in appropriate phase with translation initiation and termination sequences, and preferably, a leader sequence capable of directing secretion of the translated protein into the periplasmic space or extracellular medium. Optionally, the sequence can encode a fusion Beta R1 protein which includes an N-terminal or C-terminal peptide or tag that stabilizes or simplifies purification of the expressed recombinant product. Representative examples of such tags include sequences which encode a series of histidine residues, the Herpes simplex glycoprotein D, or glutathione S-transferase.

Suitable hosts cells include, for example, bacterial cells, such as E coli, fungal cells, such as yeast; and animal cells such as Chinese Hamster Ovary cells. Host cells are transformed with the expression vectors of this invention and cultured in conventional nutrient media. The media may contain additional compounds, such as for example compounds that induce promoters, such as for example isopropyl-β-D-thiogalactoside which induces the Lac promoter, or compounds, such as for example, ampicillin, which allows for selection of transformants.

In addition to serving as a template in the production of the Beta R1 polypeptide, the polynucleotide which encodes Beta R1 polypeptide is useful as a probe for isolating a human gene which encodes a polypeptide that is highly homologous to the Beta R1 polypeptide or a gene of an organism other than human, wherein the gene encodes a polypeptide highly homologous with the Beta R1 polypeptide of SEQ. ID. NOs. 2 or 3. The Beta R1 polynucleotide or smaller portions thereof, such as for example oligonucleotides of 200 to 2000 nucleotides can also be radiolabeled and used as hybridization probes for comparing the potency of putative IFN-β mimics. A radiolabeled DNA molecule comprising from 200 to 500 nucleotides and comprising a sequence which is at least 95% identical to or complementary to the ORF sequence shown in FIG. 4 and is useful in hybridization assays for measuring Beta R1 mRNA levels in cultured cells that have been treated with IFN-β mimics or IFN-β inhibitors.

The Beta R1 Promoter

In accordance with another aspect of the present invention an isolated polynucleotide that comprises a Beta R1 promoter sequence is provided. A promoter is a DNA regulatory region capable of binding RNA polymerase and initiating transcription of a downstream (i.e., in the 3' direction) coding sequence. The Beta R1 promoter sequence, as used herein, means the promoter sequence that naturally regulates transcription of the coding sequence for the Beta R1 polypeptide in animal cells, preferably mammalian cells, more preferably human cells. The Beta R1 promoter sequence comprises a transcription start signal sequence, an ISRE enhancer element, a gamma-activated sequence ("GAS"), a phosphorylated nuclear factor of activated T cells ("NF-Atp") element, an activator protein-1 ("AP-1") element, a TATA box, a nuclear factor-kappa-β ("NF-kB" element), and a CAAT element. A consensus sequence, as currently recognized in the art, for each of these components is shown below in Table 1.

TABLE 1

CONSENSUS SEQUENCES OF ELEMENTS PRESENT IN BETA R1 PROMOTER

| ELEMENT | SEQUENCE |
| --- | --- |
| GAS | TTNNNNNAA-3', SEQ. ID. NO. 14 |
| ISRE | 5'-RGGAAANNGAAACT-3, SEQ. ID. NO. 15 |
| NF-ATp | 5'-GGAAA-3' |
| AP-1 | 5'-TKAGTCA-3' |
| NF-kB | 5'-GGGRATYYCC-3', SEQ. ID. NO. 16 |
| TATA | 5'-TATAAT |
| CAAT | 5'-GGYCAATCT |

Preferably, starting at the 5' end of the promoter sequence, the elements are in the following order: GAS, ISRE, NF-ATp, AP-1, NF-kB, TATA, CAAT. More preferably, the Beta R1 promoter sequence, starting at the 5' end thereof, comprises the following sequences in sequential order:

(a) 5'-TTCTAGGAA;

(b) 5'-GGGTTTTCA-3';

(c) 5'-ACAAAACAGAAACT-SEQ. ID. NO. 5;

(d) 5'-TGACTCA-3';

(e) 5'-GGGAAATTCC'3', SEQ. ID. NO. 6;

(f) 5' TATAAA-3'; and (g) 5' CAAT-3'.

Figure 3A:
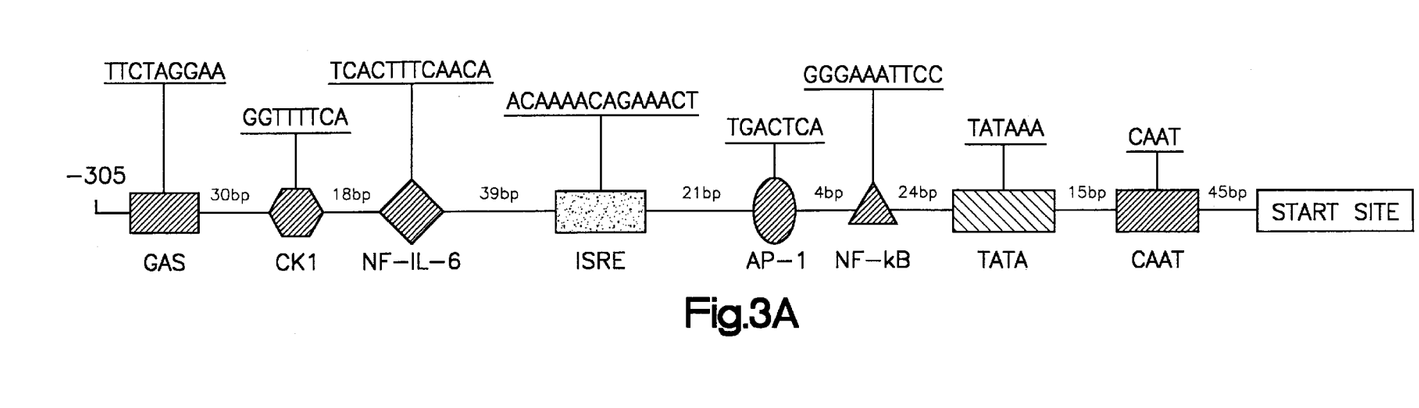
FIG. 3A is a schematic representation of the human Beta R1 promoter.

A schematic representation of this promoter sequence is shown in FIG. 3A.

Figure 3B:
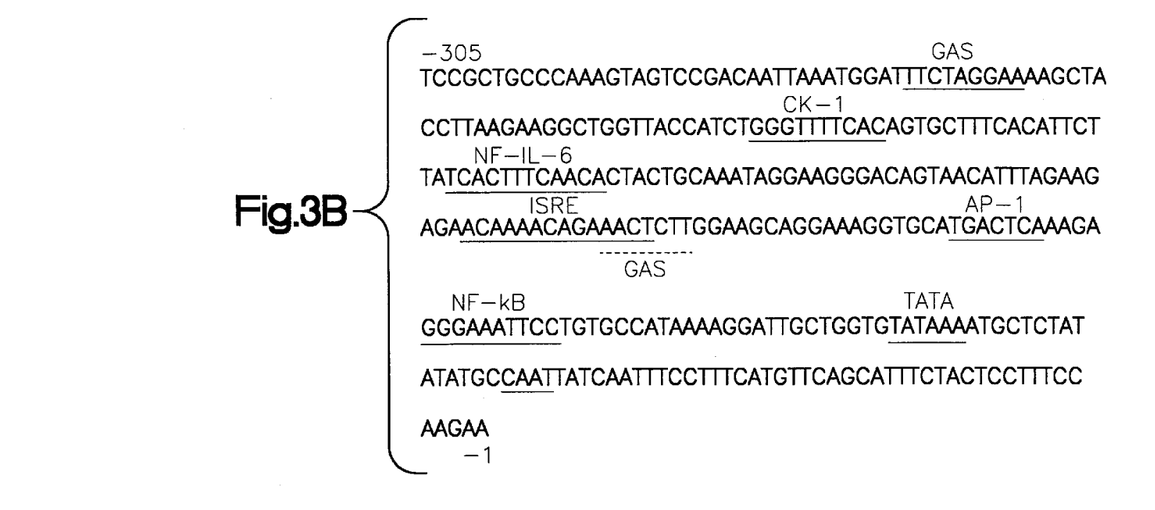
FIG. 3B depicts the human Beta R1 promoter sequence, SEQ ID NO: 4.

In one embodiment, the Beta R1 promoter sequence comprises the nucleotide sequence depicted in FIG. 3B, SEQ. ID. NO 4. In other embodiments, the Beta R1 promoter sequence comprises a sequence that encodes an ISRE and has at least 85%, preferably 90%, more preferably 95% identity or complementarity to the sequence depicted in FIG. 3B, SEQ. ID. NO.4.

The Beta R1 promoter, when operatively linked to a polynucleotide which encodes an assayable product provides a system that selectively responds to induction by IFN-β as compared to IFN-α and thus is useful for screening potential IFN-β inhibitors, agonists, and mimics. The system is also useful for quantifying the amount of IFN-β in a sample.

The Beta R1 promoter can be synthetically produced using nucleic acid synthesizers. Alternatively, the Beta R1 promoter can be made by PCR amplification of a DNA molecule having the sequence shown in FIG. 3B, SEQ. ID. NO. 4, as a template and a forward primer of 15 to 30 nucleotides that comprise a sequence that is identical to the 5' end of the sequence depicted in FIG. 3B and a reverse primer of 15 to 30 nucleotides that comprises a sequence complementary to the 3' end of the sequence depicted in FIG. 3B. Preferably the primers also comprise a sequence which encodes a restriction site on the 5' and 3'ends thereof to allow cloning of the promoter into an expression vector.

The System for Screening IFN-β Mimics.

In another aspect, the present invention provides a system for screening IFN-β mimics or for quantifying the amount of IFN-β in a sample. The system comprises a polynucleotide comprising the Beta R1 promoter sequence operatively linked to a reporter gene sequence. As used herein a reporter gene is a gene that encodes an assayable product. Suitable reporter genes include for example, the luciferase gene, the B-galactosidase gene, the chloramphenicol transferase gene, and the green fluorescent protein gene. Preferably, the polynucleotide is present in a vector that also comprises an origin of replication and a selectable marker.

Preferably, the system is made by cloning the Beta R1 promoter sequence into a vector comprising the reporter gene sequence or by cloning the reporter gene sequence into a vector comprising the Beta R1 promoter sequence, using conventional recombinant techniques. The DNA sequence encoding the Beta R1 promoter is incorporated into the vector in appropriate frame with the reporter gene sequence such that induction of the promoter causes expression of the reporter gene.

To screen IFN-β mimics or to quantify the amount of IFN-β in a sample, the system is introduced into cultured host cells that have a IFN-β receptor on the surface thereof. Preferably the cells also include the tyrosine kinase TYK2, which was described by Wilks, A. F. et al. in Mol. Cell Biol. 11:2057–2065, 1991. Suitable host cells include for example, epithelial cells, fibroblast cells, fibrosarcoma cells, and astrocytoma cells, all of which are available from ATCC. The cells may be transiently transfected with the system. Suitable methods for transiently transfecting host cells include, for example, $CaPO_4$, DEAE dextran mediated transfection, or electroporation. The cells may be stably transformed with the system. With respect to eucaryotic cells, a stably transformed cell is one in which the system has become integrated into the chromosome so that it is inherited by daughter cells through chromosome replication. Thereafter, cultures of the transiently transfected cells or stably transformed cells are treated with the putative IFN-β mimic or with the sample. The expression of the reporter gene is assayed and compared to the expression of the reporter gene in cultures treated with known amounts of IFN-β. Preferably, the cultured cells are concomitantly treated with TNF-α to enhance the amount of signal produced.

To screen IFN-β inhibitors, host cells are either transiently transfected or stably transformed with the system as described above. Thereafter, cultures of the transfected or transformed cells are treated with the proposed IFN-β inhibitor and with IFN-β The amount of signal produced in the cultures treated with the proposed IFN-β inhibitor and with IFN-β is compared to the amount of signal produced in cultures treated with IFN-β alone to determine the extent of inhibition of the IFN-β response.

The following examples of methods of making and using the products and processes of the present invention are for purposes of illustration only and are not intended to limit the scope of the claims which are appended hereto.

EXAMPLE 1

Cloning the cDNA of β-R1

Example 1a

A CRT astrocytoma cell line derived from a grade IV human astrocytoma was grown to 70–80% confluency in RPM1 1640 medium supplemented with 5 mM L-glutamine and 10% fetal bovine serum obtained from Life Technologies, Inc. MD. The cultures were treated with 100 IU/mL of IFN-γ ($1.9 \times 10^7$ IU/mg protein) obtained from Genentech, Inc. South San Francisco, Calif., for 16 hours. Total cellular RNA was isolated from cells treated with the IFN-γ and from untreated cells, using the TRIzol reagent from Life Technologies, Inc., Gaithersburg, Md., according to the method described in Chomczynski, P. and Sacchi., N, 1987, Anal. Bichem, 62:156–159. RNA isolated from the IFN-γ treated cells and from untreated cells was subjected to RNA fingerprinting using the arbitrary primed polymerase chain reaction (PCR)as described in Welsh et al., 1992, Nucleic Acids Res. 20:4965–4970, with the following modifications. The RNA, at a concentration of 5–10 μg/mL was reverse transcribed using primer zf-8 having the sequence 5' CCAGAGAGAAACCCACCA-3', SEQ. ID. NO 7. Primer zf-8 was also used for second-strand synthesis. Aliquots of the reaction product were amplified by PCR, using primers zf-8; zf-9 having the sequence 5'-CAGAGAGAAACCCACCCAG-3', SEQ.ID. NO. 8; zf-10, having the sequence 5'-AGAGAGAAACCCACCAGA-3', SEQ. ID NO. 9; and zf-11: 5, having the sequence GAGAGAAACCCACCAGAG-3', SEQ. ID. NO. 10, in the presence of [$^{32}P$]dCTP. The radiolabeled PCR products were separated on 4% sequencing gels that were then dried onto 1-mm Whatman filter paper and subjected to autoradiography. Bands of interest, i.e., bands correlative with signals in the autoradiogram of PCR products from the IFN-treated cells and absent from the autoradiogram of PCR products from the untreated cells were excised from the dried gel, and the cDNA was eluted overnight in 10 mM Tris-HCl and 1 mM EDTA. An aliquot of the gel-isolated cDNA was amplified by PCR, with the oligonucleotide primers used to generate the fingerprint. Amplified cDNAs were gel purified and stored at –20° C. for subcloning into plasmid, pGEM-T, obtained from Promega, Madison, Wis. For each PCR product, 6–10 independently isolated plasmids were sequenced using vector primers and the Sequenase reagent kit obtained from U.S. Biochemical Corp., Cleveland, Ohio. One of the plasmids, designated pB-R1-15, carried a 468-bp partial cDNA fragment. Sequence analysis of the 468-bp cDNA fragment revealed a single open reading frame (ORF) sequence of 303 base pairs. The deduced amino acid sequence of the ORF sequence indicated that it encoded a Beta R1-prepolypeptide. pB-R1-15 was deposited with the American Type Culture Collection (ATCC), 10801 University Boulevard, Manassas, Va. 20110-2209, on Aug. 28, 1997. The accession number of this deposit is ATCC Designation 209227.

Example 1b

Figure 1B:
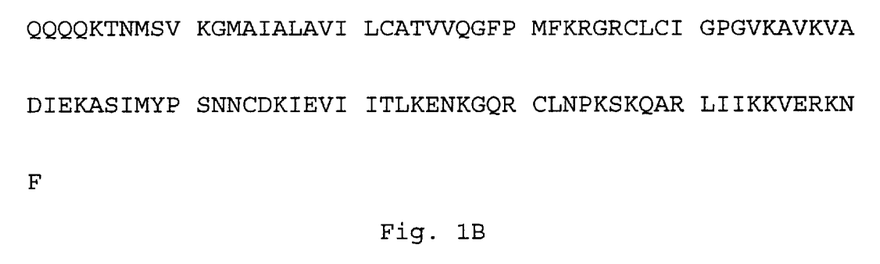
FIG. 1B depicts the amino acid sequence, SEQ ID NO: 2 of a human Beta R1 prepolypeptide.
Figure 2:
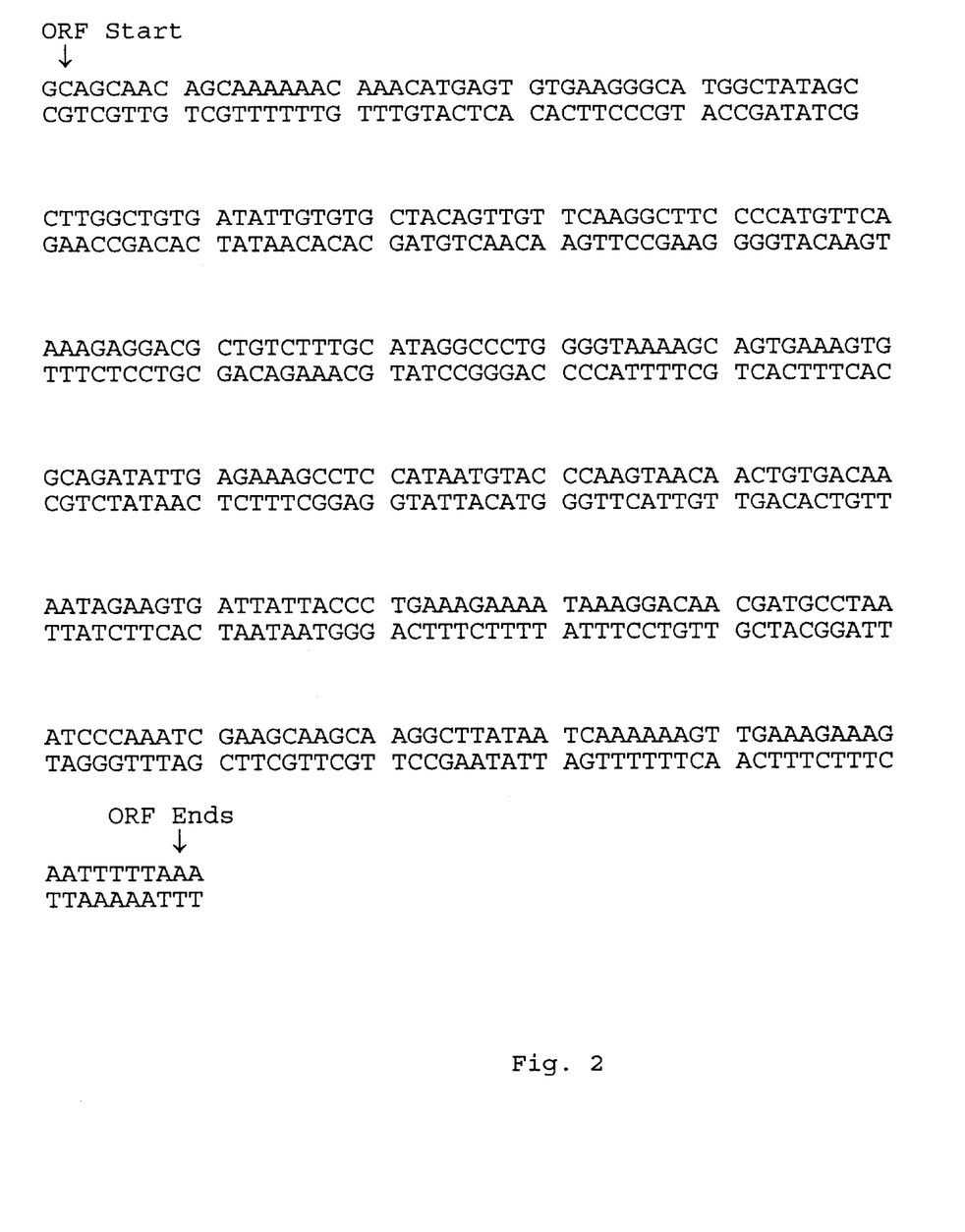
FIG. 2 depicts the sequence, SEQ ID NO: 1, of a polynucleotide that encodes a human Beta R1 polypeptide.

The fibroblast cell line wt-5, obtained from Sandra Pelligrini of the Institut Pasteur, INSERM, Paris, was grown to 70–80% confluency in Dulbecco's Minimal Essential Medium (DMEM) supplemented with 10% calf serum and treated with IFN-β at a concentration of 1000 IU/mL for 16 hours. Thereafter, poly(A)+RNA was isolated from the cells using an RNA isolation kit from Promega, Madison, Wis., according to the manufacturer's instructions. A cDNA library was prepared from a portion of the poly(A)+RNA using the ZAP Express cDNA synthesis kit from Stratagene, La Jolla, Calif., according to the manufacturer's instructions. Specifically, 5 micrograms of poly(A)$^+$ RNA was used to synthesize first strand cDNA, using oligo (dT) primers. Cloning linkers were added to both ends of oligo (dT)-primed cDNA. The cDNA with linkers was then purified and ligated to the EcoR1 -ZhoI site of the restriction enzyme-digested ZAP-EXPRESS VECTOR. The ligation products were packaged into phage which were then used to infect bacterial cells XL1-Blue MRF'. The infected cells were plated out on NZY plates. The phage DNA was recovered from the plates and screened using a radiolabeled, 468 base pair fragment of the Beta R1 cDNA contained in pB-R1-15, as a probe (hereinafter referred to as the "Beta R1 radioprobe") to confirm that the recombinant phage contained inserts of the Beta R1 gene. Phagemid vectors containing the cloned inserts were obtained from the recombinant phage by in vivo excision. The transformed bacteria were plated out on LB-kanamycin plates and positive clones identified using the Beta R1 radioprobe. The phagemid DNA was amplified by PCR using primers to the vector. The PCR products were then cloned into the cloning vector pBS from Promega according to manufacturer's instructions and the resulting recombinant plasmids used to transform *E. coli*. Plasmid DNA, designated pCB-R1-a11, was isolated from one of the positive clones and sequenced using the Sequenace kit from US Biochemicals. Sequence analysis revealed that pCB-R1-a11 contained a 2 Kb cDNA insert comprising the nucleotide sequence shown in FIG. 4 and set forth in SEQ. ID. NO. 1 and a 306 base pair ORF sequence which encodes the amino acid sequences shown in FIG. 1A and B and set forth in SEQ. ID. Nos. 2 and 3. A deposit of pCB-R1-a11 was made with the ATCC, 10801 University Boulevard, Manassas, Va. 20110-2209, on Aug. 28, 1997. This deposit was given Accession Number 209228.

A portion of the poly(A)+RNA was also reverse transcribed to provide cDNA which was then used to determine the sequence of the region upstream of the ORF sequence. The cDNA was amplified using two primers and a polymerase chain reaction kit available under the trade name 5' RACE from Clonetech. One primer anneals to the Clonetech cDNA Adapter that is ligated to both strands of the double-stranded cDNA. The other primer is a gene specific primer having the sequence 5'-TCAGATGCCCTTTTCCAGGACT-3', SEQ. ID. NO. 11, The gene specific primer anneals to a region in the ORF. Amplification was accomplished with a Taq polymerase. The PCR products were then cloned into the cloning vector pBS from Promega, according to manufacturer's instructions, and the resulting recombinant plasmids used to transform *E. coli*. The transformed bacteria were plated out on LB-ampicillin plates and positive clones identified using the Beta R1 radioprobe.

Plasmid DNA was isolated from two positive clones and sequenced using the Sequenase kit from US Biochemicals. The plasmid DNA from both clones gave a similar start site sequence, 5'-GAG-3' which is thirty five base pairs upstream from the first codon of the Beta R1 coding sequence. The location of the start site sequence is shown by the arrow in FIG. 4.

EXAMPLE 2

Cloning the promoter of β-R1

A human genomic library obtained from Clontech, Calif. was screened according to manufacturer's instructions using the β-R1 radioprobe. A total of 7 positive plaques labeled alphabetically from A–G, were obtained. The phage DNA was isolated from plaque A and from plaque B and cleaved with restriction enzymes EcoR1 and SalI. The resulting DNA fragments were separated on a 1% agarose gel and transferred to a nylon membrane which was screened with the β-R1 radioprobe to confirm that phage DNA carried the correct DNA insert, i.e., a partial clone of the β-R1gene.

The phage DNA isolated from the positive plaques was digested with EcoRI and all the restriction fragments were ligated into a pBS cloning vector that had also been digested with EcoR1 to provide a recombinant plasmid that was used to transform bacterial cells from the *E. coli* strain JM109. The pBS vector was obtained from Stratagene. Plasmid DNA was isolated from 50 transformants, separated on a 1% agarose gel, transferred to a nylon membrane, and screened with the β-R1 radioprobe. This analysis revealed that one of the plasmids, designated pRB-R1-2, contained an insert of approximately 3 kb. The sequence of a portion of this insert was determined using the Sequence kit obtained from US Biochemicals, Cleveland, Ohio. The sequence of the 3 kb insert, comprises the Beta R1 polypeptide coding region, a large 3' untranslated region, and a 305 base pair sequence upstream of the transcription start site. This 305 base pair sequence, which is shown in FIG. 3B, SEQ.ID.NO. 4, contains motifs of a promoter including a CAAT element and a TATA box. This sequence also contains a transcription start signal sequence, an ISRE enhancer element sequence, a gamma-activated sequence ("GAS"), an NF-IL-6 response element, an NF-ATp element, an AP-1 element, and an NF-kB element. This 305 base pair sequence is referred to hereinafter as "Beta R1 Promoter A". pRB-R1-2 was deposited with the American Type Culture Collection (ATCC), 10801 University Boulevard, Manassas, Va. 20110-2209, on Aug. 28, 1997. The accession number of this deposit is 209229.

EXAMPLE 3

Preparing a Vector Comprising Beta R1 Promoter A and the Luciferase Gene

The Beta R1 promoter A was amplified by PCR using as a template and a first primer, having the sequence 5'TTGGAAGATCTAGTAGAAATG-3', SEQ. ID. NO. 12 which anneals to a sequence in the vector and introduces a Bg/II site on the 5' end of the promoter-; and a second primer, having the sequence 5'ATACGAGCTCTCCGCTGC-3', SEQ. ID. NO. 13 which anneals to a sequence in the vector and introduces a SacI site on the 3'end of the promoter sequence. The PCR product was cut with BglII and SacI, and the restriction fragments were gel purified and subcloned into the pGL3-basic vector cut with the same restriction enzymes to provide pL-BetaR1. pGL-3, which was obtained from Promega Corp., Madison, Wis., lacks a promoter but has a multiple cloning sequence immediately upstream of a sequence which encodes the firefly luciferase enzyme. The pGL-3 vector also contains an ampicillin resistance selector gene and a high copy number prokaryotic origin of replication. The ligated plasmid pL-BetaR1 was used to transform the bacterial strain JM109. The transfected bacterial cells were then cultured in M-9 minimal medium supplemented with thiamine-HCl, which selects for clones that contain the F'episome. Plasmid DNA was isolated from 20 independent clones, digested with Bgl II and analyzed on a 1% agarose gel. The plasmid DNA from each of the clones contained an insert of 300 base pairs. The plasmid DNA from one of the clones was sequenced using the Sequenase kit from US Biochemicals to verify that it contained the nucleotide sequence, SEQ. ID. NO. 4, shown in FIG. 3B.

EXAMPLE 4

Screening for a Beta Interferon Response in cells Transiently Transfected with pL-BetaR1

Cells from the fibroblast cell line wt-5 were grown in seven 100 mm plates in DMEM containing 10% fetal calf serum until the cells reached 70–80% confluency. Then 20 μg of pL-BetaR1, 1.5 μg of β-galactosidase DNA, and 10 μg/mL polybrene were added to each plate and the cells incubated for 6 hours at 37° C. After incubation, the cells were subjected to DMSO shock by exposure to 30% DMSO in DMEM for 90 seconds. The cells were then washed, and incubated in DMEM and 10% fetal calf serum overnight to allow the cells to recover from DMSO shock. The next day cells from each of the seven plates were divided equally and redistributed into two plates to provide seven pairs of plates containing the transfected cells. One of following seven compounds or mixtures of compounds was added to the medium of one of the fourteen plates containing the transfected cells: 1000 IU/mL IFN-α; 1000 IU/mL IFN-β; 500 IU/mL IFN-γ; 100 ng/ml TNF-α; 1000 IU/mL IFN-α plus 100 ng/ml TNF-α; 1000 IU/mL IFN-β plus 100 ng/ml TNF-α; 500 IU/mL IFN-γ plus 100 ng/ml TNF-α. The transfected cells in the remaining seven plates were used as controls and incubated in medium alone. Following a 16 hour incubation, the cells in each of the plates were lysed by incubation for 15 minutes at room temperature in a lysis buffer provided in the luciferase assay kit which was obtained from Promega Corp., Madison, Wis. The cell lysates were then scraped from the plate and debris was removed by a brief centrifugation. The β-galactosidase activity in the cell lysates from each of the plates was assayed using the Galacto-Light Plus Assay System from Tropix Inc., Bedford, Mass. according to manufacturer's instructions and the cell lysates were normalized for transfection efficiency. The luciferase activity in the normalized cell lysates was assayed using components of a luciferase assay kit from Promega Corp, Madison, Wis., according to manufacturer's instructions. Generally, a buffer containing luciferin and ATP was added to the cell lysate at room temperature and the amount of light released from each of the lysates was measured in a Luminometer from Dynatech Laboratories, Chantily, Va.

Figure 5:
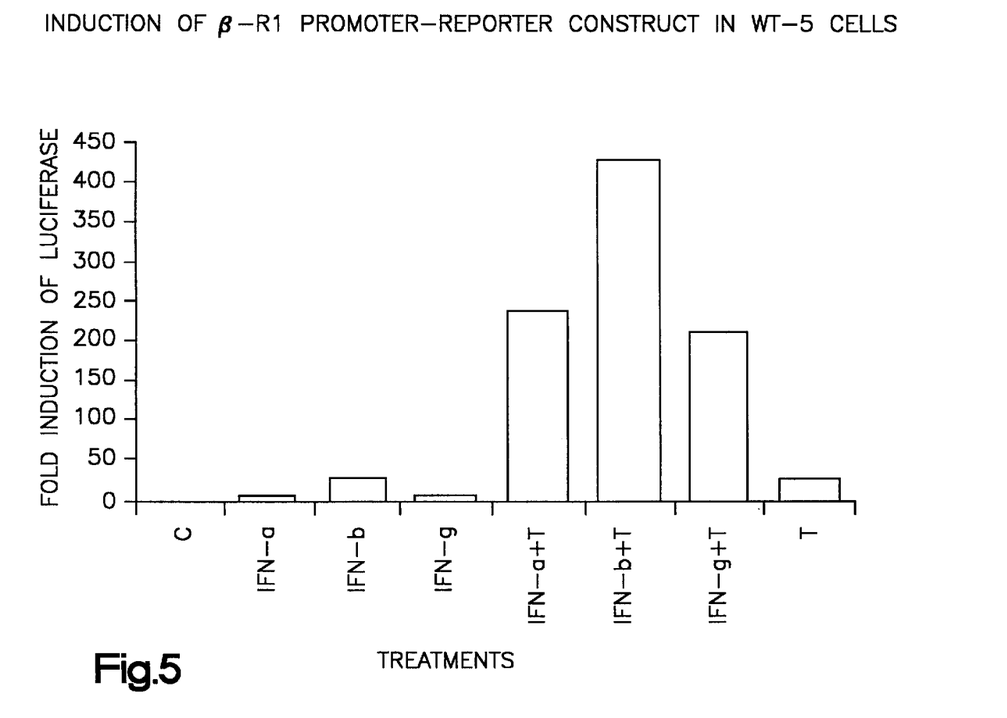
FIG. 5 shows the amount of signal produced when cells transfected with a plasmid containing a human Beta R1 promoter sequence operatively linked to the luciferase gene are treated with IFN-$\beta$, IFN-$\alpha$, IFN-$\gamma$, TNF-$\alpha$, and combinations thereof.

The results, normalized for transfection efficiency are shown in FIG. 5. As shown in FIG. 5, a strong signal was observed when wt-5 cells transiently transfected with pLBetaR1 were treated with IFN-β. The signal was even stronger in cells that had been treated with both IFN-β and TNF-α. In contrast, the signal was considerably weaker in cells treated with IFN-α, IFN-γ or TNF-α alone. Cells treated with a combination of TNF-α and IFN-α or with a combination of TNF-α and IFN-γ also exhibited a weaker signal that cells treated with a combination of TNF-α and IFN-β. These results indicate that vectors contain a polynucleotide comprising a Beta R1 promoter operatively linked to a reporter gene are useful tools for screening the IFN-β response.

EXAMPLE 5

Screening for the IFN-β-Response Using Probes Derived from the Beta R1 Gene

Fibroblast cells at 70–80% confluency were treated with IFN β at a concentration of 1000 IU/ml for 16 hours. RNA was then isolated from the cells using TriZol method. Aliquots of RNA from interferon-treated and untreated cultures were electrophoresed on a 1% agarose gel, transferred to nitrocellulose, reacted with the Beta R1 radioprobe, and the presence of the bound probe visualized by autoradiography. The hybridization signal of the Beta R1 radioprobe was quantitated with a storage phosphor technique, using a PhosphorImager (Molecular Dynamics, Sunnyville, Calif.).

The results revealed a single transcript of approximately 2.0 kilobases that accumulated to high levels after induction with IFN-β. A similar transcript was not detected in untreated cells. Thus, radiolabeled DNA molecules comprising portions of the nucleotide sequence which encodes the Beta R1 chemokine are useful for monitoring the IFN β response.

What is claimed is:

1. An isolated polynucleotide comprising a sequence encoding a Beta R1 polypeptide, said Beta R1 polypeptide encoding sequence being operatively linked with a Beta R1 promoter which is inducible by interferon Beta;
   wherein said Beta R1 polypeptide comprises the amino acid sequence set forth in SEQ ID NO: 2 or SEQ ID NO: 3;
   wherein said Beta R1 promoter comprises a sequence which is at least 95% identical to the sequence set forth in SEQ ID NO: 4, and which, starting at the 5' end thereof, sequentially comprises the following:
   (a) a gamma-activated sequence;
   (b) an ISRE enhancer element;
   (c) an NF-ATp element;
   (d) an AP-1 element
   (e) an NF-kB element;
   (f) a TATA box; and
   (g) a CAAT element.

2. The polynucleotide of claim 1 wherein
   said gamma activated sequence comprises the sequence 5'-TTCTAGGAA-3';
   said ISRE enhancer element comprises the sequence 5'-ACAAAACAGAAACT-3', SEQ. ID. NO. 5;
   said AP-1 element comprises the sequence 5'-TGACTCA-3'
   said NF-kB element comprises the sequence 5'-GGGAAATTCC-3', SEQ. ID. NO. 6: and
   wherein said gamma activated sequence, said ISRE enhancer element, said AP-1 element, said NF-ATp element, and said NF-kB element are located in a sequence which is 303 base pairs in length.

3. The polynucleotide of claim 1 wherein said polynucleotide comprises a nucleotide sequence encoding a Beta R1 polypeptide comprising the amino acid sequence as set forth in SEQ.ID.NO. 2.

4. The polynucleotide of claim 1 wherein the nucleotide sequence encodes a polypeptide comprising the amino acid sequence as set forth in SEQ.ID.NO. 3.

5. The polynucleotide of claim 4 comprising nucleotide 104 to nucleotide 409 as set forth in SEQ. ID. NO. 1.

6. An isolated polynucleotide comprising a Beta R-1 polypeptide encoding sequence operatively linked with a Beta R1 promoter, said Beta R1 promoter being inducible by interferon Beta; wherein said Beta R1 promoter comprises a sequence which at least 95% identical to the sequence set forth in SEQ ID NO: 4, and wherein said Beta R1 promoter sequence, starting at the 5' end thereof, sequentially comprises the following:
   (a) a gamma-activated sequence;
   (b) an ISRE enhancer element;
   (c) an NF-ATp element;
   (d) an AP-1 element
   (e) an NF-kB element;
   (f) a TATA box; and
   (g) a CAAT element; and
   wherein said Beta R1 polypeptide encoding sequence is selected from the group consisting of:
   (a) a Beta R1 polypeptide encoding sequence as contained in pB-R1-a11, ATCC Deposit No. 209227 and
   (a) a Beta R1 polypeptide encoding sequence as contained in pCB-R1-a11, ATCC Deposit No. 209228.

7. An isolated polynucleotide comprising a sequence encoding a Beta R1 polypeptide functionally associated with a Beta R1 promoter sequence; wherein said Beta R1 polypeptide comprises the amino acid sequence set forth in SEQ ID NO: 2 or SEQ ID NO: 3; and wherein said Beta R1 promoter sequence comprises the nucleotide sequence set forth in SEQ ID NO: 4.

8. The isolated polynucleotide of claim 7 wherein said Beta R1 polypeptide encoding sequence comprises the sequence set forth in SEQ ID NO: 2.

9. The isolated polynucleotide of claim 7 wherein said Beta R1 polypeptide encoding sequence comprises the sequence set forth in SEQ ID NO: 3.

10. An isolated polynucleotide comprising a Beta R-1 polypeptide encoding sequence functionally associated with a Beta R1 promoter; wherein said Beta R1 promoter comprises the sequence set forth in SEQ ID NO: 4, and wherein said Beta R1 polypeptide encoding sequence is selected from the group consisting of: the Beta R1 polypeptide encoding sequence as contained in pB-R1-a11, ATCC Deposit No. 209227 and the Beta R1 polypeptide encoding sequence as contained in pCB-R1-a11, ATCC Deposit No 209228.

11. The isolated polynucleotide of claim 10 wherein said Beta R1 encoding sequence is the Beta R1 encoding sequence as contained in pB-R1-a11, ATCC Deposit 209227.

12. The isolated polynucleotide of claim 10 wherein said Beta R1 encoding sequence is the Beta R1 encoding sequence as contained in pCB-R1-a11, ATCC Deposit No 209228.

* * * * *

UNITED STATES PATENT AND TRADEMARK OFFICE
CERTIFICATE OF CORRECTION

PATENT NO. : 5,977,334
DATED : November 2, 1999
INVENTOR(S) : Richard Ransohoff, Sandhya Rani It is certified that error appears in the above-identified patent and that said Letters Patent is hereby corrected as shown below:

On the title page,

In the Abstract, after astrocytes, please delete "a" and insert -- and --.

In claim 2, line 59, after 6 please delete ":" and insert -- ; --.

Signed and Sealed this

Ninth Day of May, 2000

Attest:

Attesting Officer

Q. TODD DICKINSON

Director of Patents and Trademarks

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 758 base pairs
      (B) TYPE: nucleic acid
      (C) STRANDEDNESS: double
      (D) TOPOLOGY: linear    (ii) MOLECULE TYPE: cDNA    (iii) HYPOTHETICAL: NO    (iv) ANTI-SENSE: NO    (ix) FEATURE:
      (A) NAME/KEY: CDS
      (B) LOCATION: 104..409

(xi) SEQUENCE DESCRIPTION: SEQ ID NO:1:

```
CANAACTGGA CTCGCGCGCC TGCAGGTCGA CACTAGTGGA TCCAAAGAAT TCGGCACGAG        60

CCAAGAAAGA GCAGCAAAGC TGAAGTAGCA GCAACAGCAC CAGCAGCAAC AGCAAAAAAC       120

AAACATGAGT GTGAAGGGCA TGGCTATAGC CTTGGCTGTG ATATTGTGTG CTACAGTTGT       180
```

-continued

```
TCAAGGCTTC CCCATGTTCA AAAGAGGACG CTGTCTTTGC ATAGGCCCTG GGGTAAAAGC      240

AGTGAAAGTG GCAGATATTG AGAAAGCCTC CATAATGTAC CCAAGTAACA ACTGTGACAA      300

AATAGAAGTG ATTATTACCC TGAAAGAAAA TAAAGGACAA CGATGCCTAA ATCCCAAATC      360

GAAGCAAGCA AGGCTTATAA TCAAAAAAGT TGAAAGAAAG AATTTTTAAA AATATCAAAA      420

CATATGAAGT CCTGGAAAAG GGCATCTGAA AAACCTAGAA CAAGTTTAAC TGTGACTACT      480

GAAATGACAA GAATTCTACA GTAGGAAACT GAGACTTTTC TATGGTTTTG TGACTTTCCA      540

CTTTTGTTCA GTTATTTGAA GGATGAAAGG TGGGTGAAAG GACCCAAAAC NGAAATACGT      600

CTCCCTGAAT GAATGACAAT CCGAATCCNC TGCCCCAAAG AATCCCACNA TTTAATGGAT      660

TCNTAGGAAA ACTACCTTAN AAAGGCNGGT TACCTCCGAA TTTACCAAGT GCNTCCCTTT      720

CCTACTGTTC TTTTATACTT CCNGCNTTCC TAGGCNAN                              758
```

(2) INFORMATION FOR SEQ ID NO:2:

(i) SEQUENCE CHARACTERISTICS:
        (A) LENGTH: 101 amino acids
        (B) TYPE: amino acid
        (C) STRANDEDNESS: single
        (D) TOPOLOGY: linear     (ii) MOLECULE TYPE: peptide     (iii) HYPOTHETICAL: NO     (iv) ANTI-SENSE: NO     (xi) SEQUENCE DESCRIPTION: SEQ ID NO:2:

```
Gln Gln Gln Gln Lys Thr Asn Met Ser Val Lys Gly Met Ala Ile Ala
  1               5                  10                  15

Leu Ala Val Ile Leu Cys Ala Thr Val Val Gln Gly Phe Pro Met Phe
             20                  25                  30

Lys Arg Gly Arg Cys Leu Cys Ile Gly Pro Gly Val Lys Ala Val Lys
         35                  40                  45

Val Ala Asp Ile Glu Lys Ala Ser Ile Met Tyr Pro Ser Asn Asn Cys
     50                  55                  60

Asp Lys Ile Glu Val Ile Ile Thr Leu Lys Glu Asn Lys Gly Gln Arg
 65                  70                  75                  80

Cys Leu Asn Pro Lys Ser Lys Gln Ala Arg Leu Ile Ile Lys Lys Val
                 85                  90                  95

Glu Arg Lys Asn Phe
            100
```

(2) INFORMATION FOR SEQ ID NO:3:

(i) SEQUENCE CHARACTERISTICS:
        (A) LENGTH: 83 amino acids
        (B) TYPE: amino acid
        (C) STRANDEDNESS: single
        (D) TOPOLOGY: linear     (ii) MOLECULE TYPE: peptide     (iii) HYPOTHETICAL: NO     (iv) ANTI-SENSE: NO     (xi) SEQUENCE DESCRIPTION: SEQ ID NO:3:

```
Val Ile Leu Cys Ala Thr Val Val Gln Gly Phe Pro Met Phe Lys Arg
  1               5                  10                  15
```

```
Gly Arg Cys Leu Cys Ile Gly Pro Gly Val Lys Ala Val Lys Val Ala
             20                  25                  30

Asp Ile Glu Lys Ala Ser Ile Met Tyr Pro Ser Asn Asn Cys Asp Lys
             35                  40                  45

Ile Glu Val Ile Ile Thr Leu Lys Glu Asn Lys Gly Gln Arg Cys Leu
 50                  55                  60

Asn Pro Lys Ser Lys Gln Ala Arg Leu Ile Ile Lys Lys Val Glu Arg
 65                  70                  75                  80

Lys Asn Phe
```

(2) INFORMATION FOR SEQ ID NO:4:

(i) SEQUENCE CHARACTERISTICS:
        (A) LENGTH: 303 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO         (xi) SEQUENCE DESCRIPTION: SEQ ID NO:4:

```
TCCGCTGCCC AAAGTAGTCC GACAATTAAA TGGATTTCTA GGAAAAGCTA CCTTAAGAAG    60

GCTGGTTACC ATCTGGGTTT TCACAGTGCT TTCACATTCT TATCACTTTC AACACTACTG   120

CAAATAGGAA GGGACAGTAA CATTTAGAAG AGAACAAAAC AGAAACTCTT GGAAGCAGGA   180

AAGGTGCATG ACTCAAAGAG GGAAATTCCT GTGCCATAAA AGGATTGCTG GTGTATAAAA   240

TGCTCTATAT ATGCCAATTA TCAATTTCCT TTCATGTTCA GCATTTCTAC TCCTTTCCAA   300

GAA                                                                 303
```

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: double
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:5:

```
ACAAAACAGA AACT                                                      14
```

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: double
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:6:

```
GGGAAATTCC                                                           10
```

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:7:

CCAGAGAAAC CCACCA                                      16

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:8:

CAGAGAAACC CACCCAG                                    17

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:9:

AGAGAGAAAC CCACCAGA                                 18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:10:

GAGAGAAACC CACCAGAG                                 18

(2) INFORMATION FOR SEQ ID NO:11:

(i) SEQUENCE CHARACTERISTICS:
                 (A) LENGTH: 22 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TCAGATGCCC TTTTCCAGGA CT                                                    22

(2) INFORMATION FOR SEQ ID NO:12:

(i) SEQUENCE CHARACTERISTICS:
                 (A) LENGTH: 18 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

ATACGAGCTC TCCGCTGC                                                         18

(2) INFORMATION FOR SEQ ID NO:13:

(i) SEQUENCE CHARACTERISTICS:
                 (A) LENGTH: 21 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TTGGAAGATC TAGTAGAAAT G                                                     21

(2) INFORMATION FOR SEQ ID NO:14:

(i) SEQUENCE CHARACTERISTICS:
                 (A) LENGTH: 10 base pairs
                 (B) TYPE: nucleic acid
                 (C) STRANDEDNESS: double
                 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

TTNNNNNNAA                                                                  10

(2) INFORMATION FOR SEQ ID NO:15:

(i) SEQUENCE CHARACTERISTICS:
                 (A) LENGTH: 14 base pairs
                 (B) TYPE: nucleic acid
                 (C) STRANDEDNESS: double

```
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

RGGAAANNGA AACT                                                             14

(2) INFORMATION FOR SEQ ID NO:16:

(i) SEQUENCE CHARACTERISTICS:
         (A) LENGTH: 10 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

GGGRATYYCC                                                                  10
```